(12) United States Patent
Hammer et al.

(10) Patent No.: US 10,687,857 B2
(45) Date of Patent: Jun. 23, 2020

(54) HOOK WITH ROTATING SADDLE AND ROTATABLE MONO AXIAL PEDICLE SCREW

(71) Applicant: BLACKSTONE MEDICAL, INC., Lewisville, TX (US)

(72) Inventors: Michael Hammer, Pine Brook, NJ (US); Tara Ziolo, Hewitt, NJ (US)

(73) Assignee: BLACKSTONE MEDICAL, INC., Lewisville, TX (US)

( * ) Notice: Subject to any disclaimer, the term of this patent is extended or adjusted under 35 U.S.C. 154(b) by 0 days.

(21) Appl. No.: 15/800,011

(22) Filed: Oct. 31, 2017

(65) Prior Publication Data

US 2018/0116696 A1 May 3, 2018

Related U.S. Application Data

(62) Division of application No. 13/839,946, filed on Mar. 15, 2013, now Pat. No. 9,801,664.

(51) Int. Cl.
*A61B 17/70* (2006.01)

(52) U.S. Cl.
CPC ...... *A61B 17/7032* (2013.01); *A61B 17/7037* (2013.01); *A61B 17/7056* (2013.01)

(58) Field of Classification Search
CPC ............ A61B 17/7032; A61B 17/7037; A61B 17/7056; A61B 17/7038; A61B 17/7041; A61B 17/7046
See application file for complete search history.

(56) References Cited

U.S. PATENT DOCUMENTS

| 10,258,385 | B1* | 4/2019 | Doubler | A61B 17/7032 |
| 2008/0086129 | A1* | 4/2008 | Lindemann | A61B 17/685 606/86 R |
| 2009/0105771 | A1* | 4/2009 | Lei | A61B 17/7037 606/313 |
| 2011/0098755 | A1* | 4/2011 | Jackson | A61B 17/7008 606/305 |
| 2011/0270321 | A1* | 11/2011 | Prevost | A61B 17/7002 606/305 |
| 2013/0023935 | A1* | 1/2013 | Pham | A61B 17/70 606/264 |
| 2013/0110176 | A1* | 5/2013 | Rezach | A61B 17/7037 606/305 |
| 2015/0201972 | A1* | 7/2015 | Doubler | A61B 17/7002 606/266 |
| 2015/0282844 | A1* | 10/2015 | Vedula | A61B 17/7032 606/305 |

* cited by examiner

*Primary Examiner* — Tessa M Matthews
(74) *Attorney, Agent, or Firm* — Haynes and Boone, LLP (57) ABSTRACT

Disclosed herein are a hook with rotating saddle and a rotatable mono axial pedicle screw. In an embodiment, the disclosed hook may include at least one body comprising a hook member and a saddle member. The hook member and saddle member may be rotatably mounted to one another so as to rotate with respect to each other only about a common axis, and the saddle member may be configured for connection to an end of a connecting member. A surgical screw system may include receiver and screw members engagable with one another such that when engaged, only rotation of the receiving member about the longitudinal axis of the screw member and restrain against substantially all other translational or rotational movement.

15 Claims, 10 Drawing Sheets

HOOK WITH ROTATING SADDLE AND ROTATABLE MONO AXIAL PEDICLE SCREW

CROSS-REFERENCE TO RELATED APPLICATIONS

This is a divisional application of U.S. application Ser. No. 13/839,946, which was filed on Mar. 15, 2013, and is incorporated by reference in its entirety.

TECHNICAL FIELD

This disclosure relates generally to surgical screws and hooks for use with implantation rods and more particularly to hook apparatuses having rotating saddles and to rotatable mono axial pedicle screws.

BACKGROUND

The bones and connective tissue of an adult human spinal column consists of more than 20 discrete bones coupled sequentially to one another by a tri-joint complex. The complex consists of an anterior disc and two posterior facet joints. The anterior discs of adjacent bones are cushioned by cartilage spacers referred to as intervertebral discs. The over 20 bones of the spinal column are anatomically categorized as one of four classification: cervical, thoracic, lumbar, or sacral. The cervical portion of the spine which comprises the top of the spine up to the base of the skull, includes the first 7 vertebrae. The intermediate 12 bones are thoracic vertebrae, and connect to the lower spine comprising the 5 lumbar vertebrae. The base of the spine is a sacral bones (including the coccyx).

The spinal column of bones is highly complex in that it includes the over 20 bones coupled to one another, housing and protecting critical elements of the nervous system having innumerable peripheral nerves and circulatory bodies in close proximity. Despite its complexity, the spine is a highly flexible structure, capable of a high degree of curvature and twist in nearly every direction.

Genetic or developmental irregularities, trauma, chronic stress, tumors and disease, however, can result in spinal pathologies which either limit this range of motion, or which threatens the critical elements of the nervous system housed within the spinal column. A variety of systems have been disclosed in the art which achieve this immobilization by implanting artificial assemblies in or on the spinal column. These assemblies may be classified as anterior, posterior or lateral implants. Lateral and anterior assemblies are coupled to the anterior portion of the spine which is in the sequence of vertebral bodies. Posterior implants generally comprise pairs of rods, which are aligned along the axis which the bones are to be disposed, and which are then attached to the spinal column by either hooks which couple to the lamina or attach to the transverse processes, or by screws which are inserted through the pedicles. In order to provide enhanced torsional rigidity, these implants generally include cross-connecting devices which couple the rods together transverse to the axis of the implants. These cross-connecting devices may couple directly to the rods themselves, or may be attached to the pedicle screws.

There is limited space about the spinal column for the attachment of the screws or hooks which hold in place the implant rods. Factors such as pedicle screw depth, placement and angle of insertion are taken into account when attempting to place implant rods in an optimal manner; however, there is often a trade-off between space requirements, needs inherent to the particular corrective treatment or condition involved, and structural strength and stability. For example, using multi axial pedicle screws (i.e., which allow rotation or deflection of the head thereof in multiple directions) to hold in place implant rods, facilitates surgical manipulation and placement of the rods, but lower strength, as such capacity for movement may remain post-surgery. Such movement may be desired when addressing the needs of certain patients; however, where stronger fixation is desirable concerns as to screw, hook and rod placement are nonetheless applicable. Known mono axial screws may be employed to achieve greater strength, but they do not provide the level or flexibility for manipulation to optimally place the rods as do their multi axial counterparts.

Similarly, when employing cross-linking hook members known in the art, concerns arise due to the tight quarters for placement of same, particularly if the given surgical scenario requires or would benefit from use of cross-linking members that traverse a non-linear path between adjacent rods whilst still achieving a high level of added strength and stability, and flexibility in terms ease or even possibility of installation.

It is desirable to provide pedicle screws and surgical hook apparatuses that obviate or eliminate the need to make the trade-offs described above.

BRIEF SUMMARY

An exemplary embodiment of a surgical hook apparatus may include at least one body that may include a hook member and a saddle member. The hook member and saddle member may be rotatably mounted to one another so as to rotate with respect to each other only about a common axis. The saddle member may be configured for connection to an end of a connecting member.

In an embodiment, a first one of the hook member and the saddle member, which may in an embodiment be the hook member, may be provided with a cavity defined therein for receiving a portion of a second one of the hook member and the saddle member. The apparatus may further comprise a plurality of balls, and a channel sized to the balls may be defined within the cavity in one or more of and between the hook member and saddle member. A compression member may be provided in engagement with at least one of the hook member and the saddle member to compressively retain the balls in the channel so as to rotatably mount the hook member and saddle member to one another.

In an embodiment, the compression member may comprise a spring that provides force outwardly upon the saddle member.

In another embodiment, the apparatus may further comprises a gasket, and a channel sized to the gasket may be defined within a cavity in one or more of and between the hook member and saddle member. The gasket may be provided within the channel in sliding engagement with the hook member and the saddle member so as to rotatably mount the hook member and saddle member to one another.

In an embodiment, a connecting cavity having one or more walls may be defined in the saddle member for receiving therein a first end of the connecting member. The walls may be provided with threads for engagement with complementary threads provided on the connecting member.

In an embodiment, the apparatus may further comprise a set screw mounted in a through hole in the saddle member so as to bear against the connecting member in the saddle cavity when the set screw is tightened.

In an embodiment, the connecting member may have a first end and a second end and may be connected at its first end within the receiving chamber of the saddle member.

In an embodiment, the apparatus may also include a second body joined to a second end of the connecting member.

In an embodiment, the connecting member may be non-linear. The connecting member may comprise a first segment, a second segment and a third segment. In an embodiment, the first segment may be connected to the second segment and the second segment may be connected to the third segment. In an embodiment, the first segment may be oriented substantially normal to the second segment and substantially parallel to the third segment. In another embodiment, the first segment may be oriented at a substantially 45 degree angle to the second segment and may be substantially parallel to the third segment.

According to an embodiment of the present disclosure, a surgical screw system may include a screw member that may have a head portion, a body portion and a longitudinal axis. The system may also include a receiver member that may have upper and lower portions. The upper portion may be provided with a receiving slot defined therein for receiving a surgical rod. The receiving member may be provided with a plurality of balls embedded in its surface and that may be positioned for sliding engagement with the head portion of the screw member. The receiving member may be mountable to the screw member by application of force that may be substantially in a direction parallel to the longitudinal axis and substantially towards the body portion so as to frictionally engage the balls with a receiving surface of the screw member. When mounted to the head portion the balls may be positioned so as to slide about the receiving surface and allow only rotation of the receiving member about the longitudinal axis of the screw member and to restrain against substantially all other translational or rotational movement.

In an embodiment, a complementary receiving channel may be defined in the receiving surface to receive the balls when the receiving member is mounted to the head portion.

According to an embodiment of the present disclosure, a surgical screw system may include screw member that may have a head portion, a body portion and a longitudinal axis. The system may include a receiver member having upper and lower portions. The upper portion may be provided with a receiving slot defined therein for receiving a surgical rod. The system may further comprise an annular gasket. The system may also include a channel sized to the gasket that may be defined within the surface of one or more of the receiving member and the head portion. The receiving member may be mountable to the screw member by application of force in a direction substantially parallel to the longitudinal axis and substantially towards the body portion so as to frictionally engage the gasket with a receiving surface of the screw member. When mounted to the head portion the gasket may positioned to slide against the receiving surface to allow only rotation of the receiving member about the longitudinal axis of the screw member and to restrain against substantially all other translational or rotational movement.

DETAILED DESCRIPTION

Figure 1:
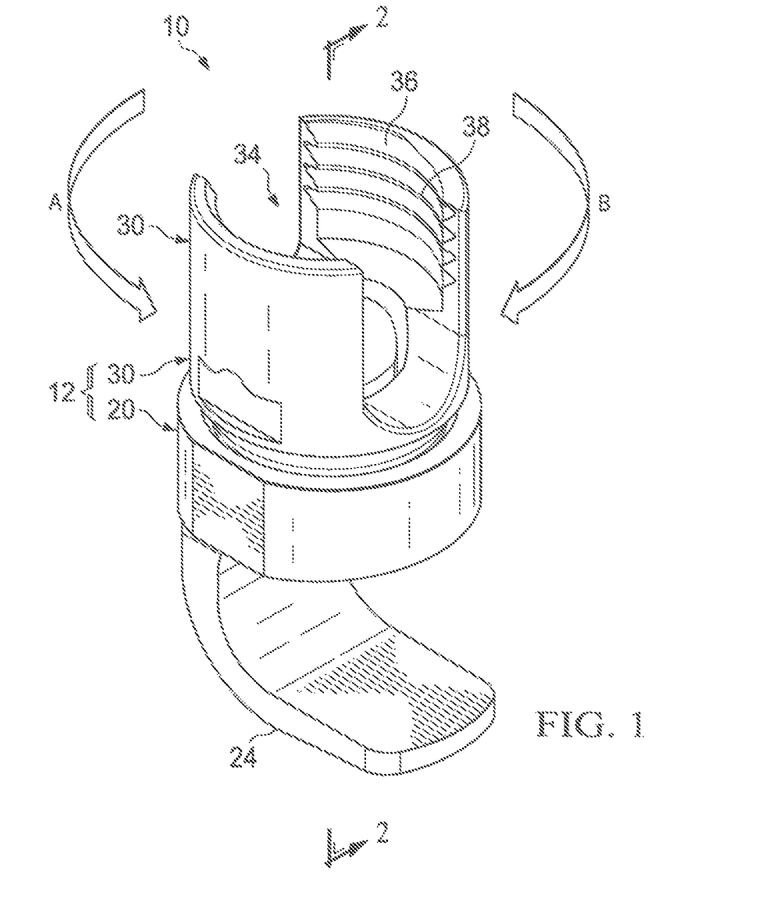
FIG. 1 illustrates an isometric view of an exemplary embodiment of a surgical hook apparatus.
Figure 6:
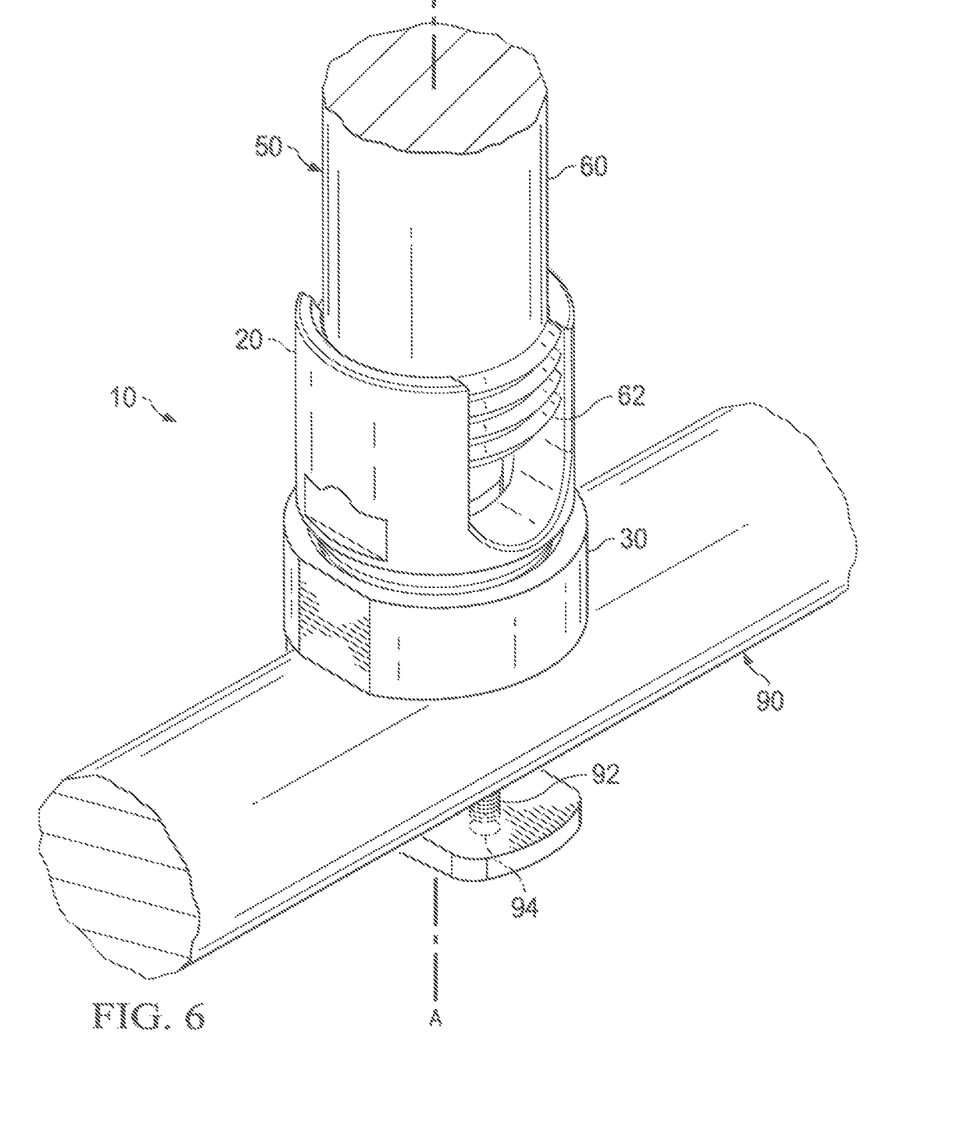
FIG. 6 illustrates an isometric view of an exemplary surgical hook apparatus, shown engaged with a pair of surgical rods.

The current disclosure enables rotating the bone attachment and rod attachment interfaces, such as the hook member 20 and saddle member 30 provided in the surgical hook apparatus shown in FIG. 1, relative to each other along a common axis A-A, shown in FIG. 6. This rotational capability facilitates controlled, secure attachment of the disclosed surgical hook apparatus 10 to bone or to connecting members 50 such as rods (see FIG. 6, for example) by way of enabling independent alignment with different attachment points of interest. Restraining other movement or rotation of the hook member 20 and saddle member 30 with respect to one another helps maintain the strength provided by systems wherein the hook and saddle do not rotate or translate with respect to one another.

Figure 7A:
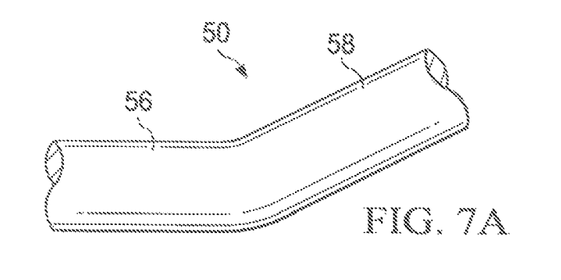
FIG. 7A illustrates an isometric view of an exemplary connecting member.
Figure 7B:
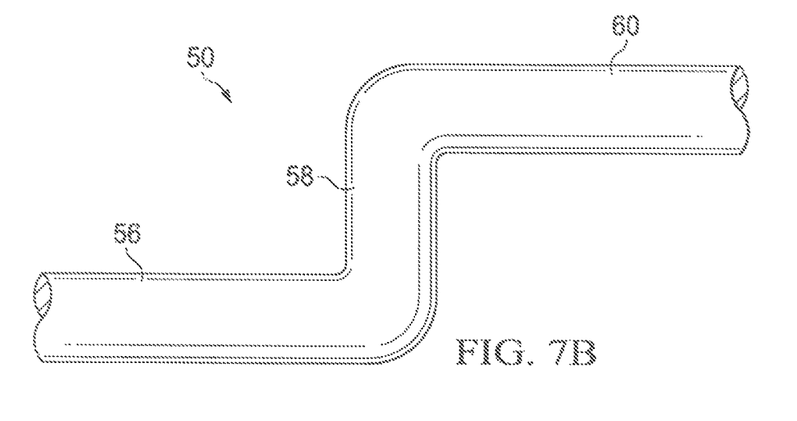
FIG. 7B illustrates an isometric view of another exemplary connecting member.
Figure 7C:
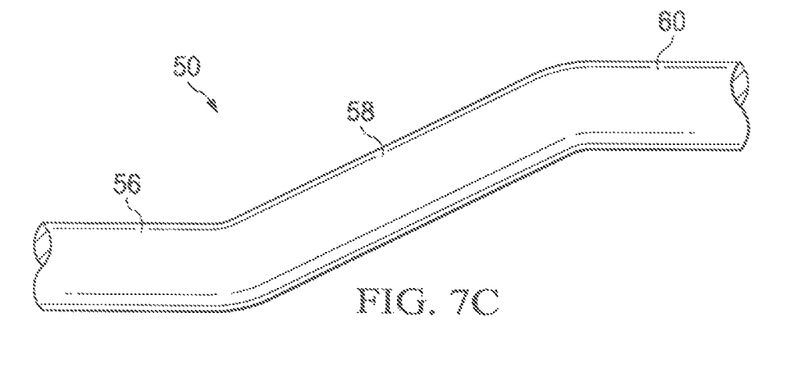
FIG. 7C illustrates an isometric view of yet another exemplary connecting member.

Looking to FIG. 1 there is illustrated an isometric view of an exemplary embodiment of a surgical hook apparatus 10 which includes a body 12. The body 12 includes a hook member 20 and a saddle member 30. The hook member 20 and saddle member 30 are rotatably mounted to one another so as to rotate with respect to each in circumferential directions shown by arrows A and B in FIG. 1, and only about a common axis A-A, shown in FIG. 6. The saddle member 30 is configured for connection to a first end 52 of a connecting member 50 as shown in FIG. 6. While illustrated as a cylindrical surgical rod, additional configurations of connecting member 50 including, for example, ones of various geometries and proportions throughout their length as may be needed in the particular surgical scenario. In addition, the connecting member 50 need not be linear. As shown in FIGS. 7A, 7B and 7C, connecting members 50 may be provided with, for example, first 56, second 58 and third 60 segments offset from or otherwise provided at various orientations to one another. Embodiments shown include a two segment connecting member 50 in FIG. 7A, and three segment connecting members 50 in FIGS. 7B and 7C, both wherein the first segment 56 is connected to the second segment 58 and the second segment 58 is connected to the third segment 60. While shown as unitary, it will be appreciated that connecting members 50 comprising discrete, joined segments may be employed to similar effect. As examples of potential orientations, in FIG. 5B, the first segment 56 is oriented substantially normal to the second segment 58 and substantially parallel to the third segment 60. In another embodiment, the first segment 56 may be oriented at a substantially 45 degree angle to the second segment 58 and may be substantially parallel to the third segment 60. It will be appreciated that numerous other arrangements and geometries of connecting member 50 are possible within the scope of the present disclosure. The capability of 360 degree rotation of the hook 20 and saddle 30 members with respect to one another as disclosed herein provides practitioners with a greater capacity to utilize implants having more complex geometries while maintaining the strength that can be lost in systems allowing for more degrees of rotational or translational freedom. For example, embodiments disclosed herein enable securing of hook members 20 to rods or other connecting members 50 that have been secured to screws (not illustrated), which typically are installed lateral to preferred hook implantation sites. Lateral offsets as disclosed herein may incorporate screw attachment geometry (for example, "D" shaped or cylindrical) and typically are oriented approximately 90 degrees to the connecting member or rod. As hook apparatuses are very often provided with a slot to accept an implantation rod in a cephalad-caudal orientation, such a slot needs to be oriented medial-lateral (i.e., approximately 90 degrees from their normal orientation). By allowing the saddle member 30 and hook member to rotate 360 degrees with respect to one another on a common axis A-A, the hook member 20 can be joined to implant rods held in place by screws for example, by securing a lateral offset connector to the rod, and clamping the lateral offset connector's rod section in the hook apparatuses in saddle member 30. A lateral connector 50 with a cylindrical rod section in combination with a hook apparatus 10 with a rotating saddle member 30 can mimic the function of the less stable but more adaptable multi-axial variants of a hook apparatus by way of rotating the laterally offset section via rotation of the hook member 20 relative to the saddle member 30 enables the disclosed apparatus 10 to mimic the function of less stable but typically more adaptable multi-axial hook apparatuses.

Figure 2:
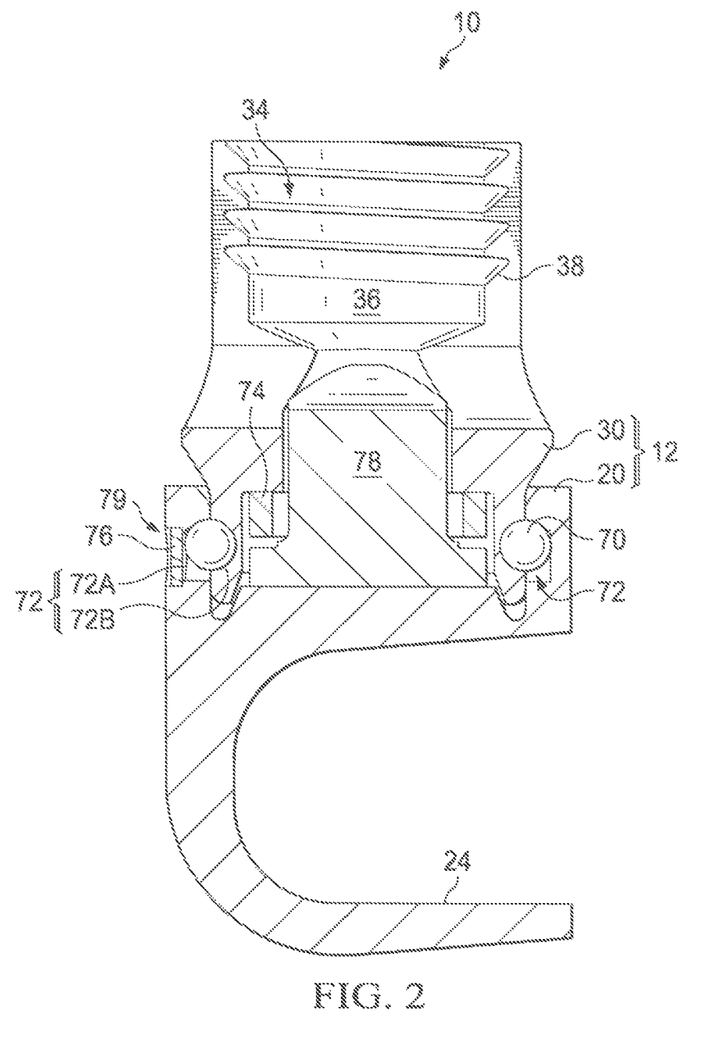
FIG. 2 illustrates a sectional view of the surgical hook apparatus of FIG. 1, taken along line 2-2.
Figure 3:
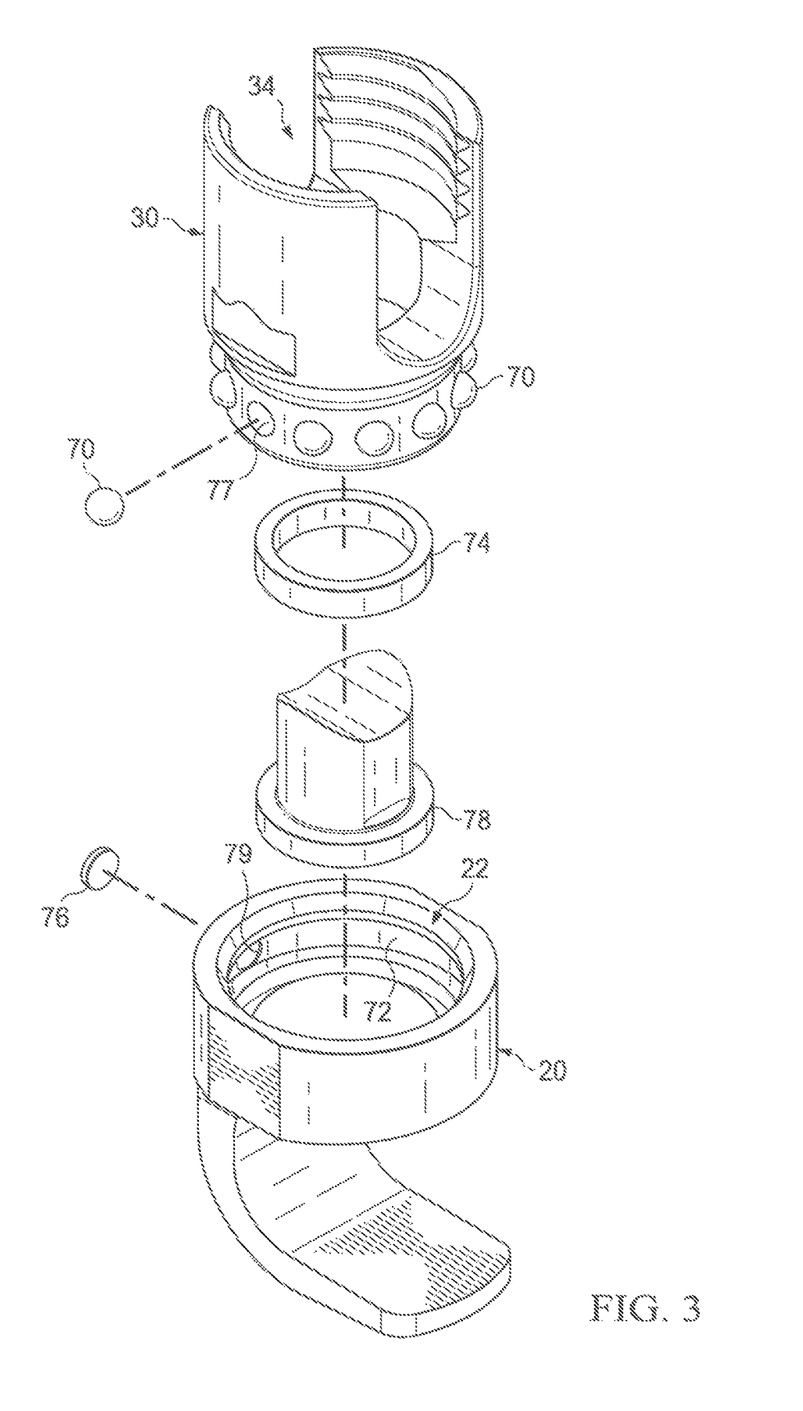
FIG. 3 illustrates a partially exploded view of the surgical hook apparatus shown in FIG. 1.

The hook member 20 is shown in FIGS. 1 through 3 with a cavity 22 defined therein. The cavity 22 is shaped and configured to receive a portion 32 of the saddle member 30. While the hook 20 and saddle 30 members are shown in a male-female engagement wherein the saddle member 30 is the male component, it will be appreciated that the opposite configuration is possible whilst still achieving the advantageous, stable, strong rotational functionality disclosed herein.

An exemplary configuration of the hook 20 and saddle 30 members includes a plurality of balls 70, as shown in FIGS. 2 and 3. A channel 72 is defined within the cavity 22 and may be made up of one or more channel portions 72A, 72B defined in each of the hook 20 and saddle 30 members. A compression member such as a spring 74 is engaged with saddle member 30 to compressively retain the balls 70 in the channel 72, thereby rotatably mounting the hook member 20 and saddle member 30 to one another. While shown in FIG. 2 as providing force outwardly upon the saddle member to achieve such compression, it will be appreciated compression members providing inwardly directed compression upon whichever of the members 20,30 is fulfilling the female component if their interaction could likewise be employed.

Figure 4:
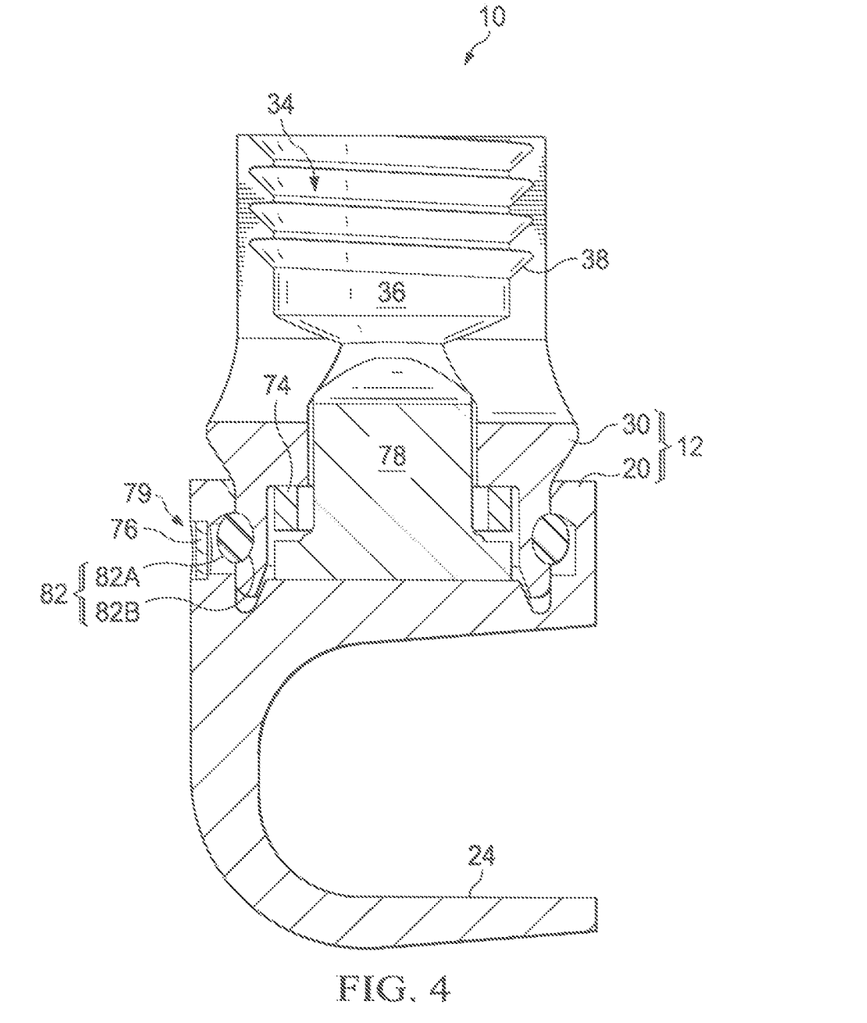
FIG. 4 illustrates a sectional view of another surgical hook apparatus.
Figure 5:
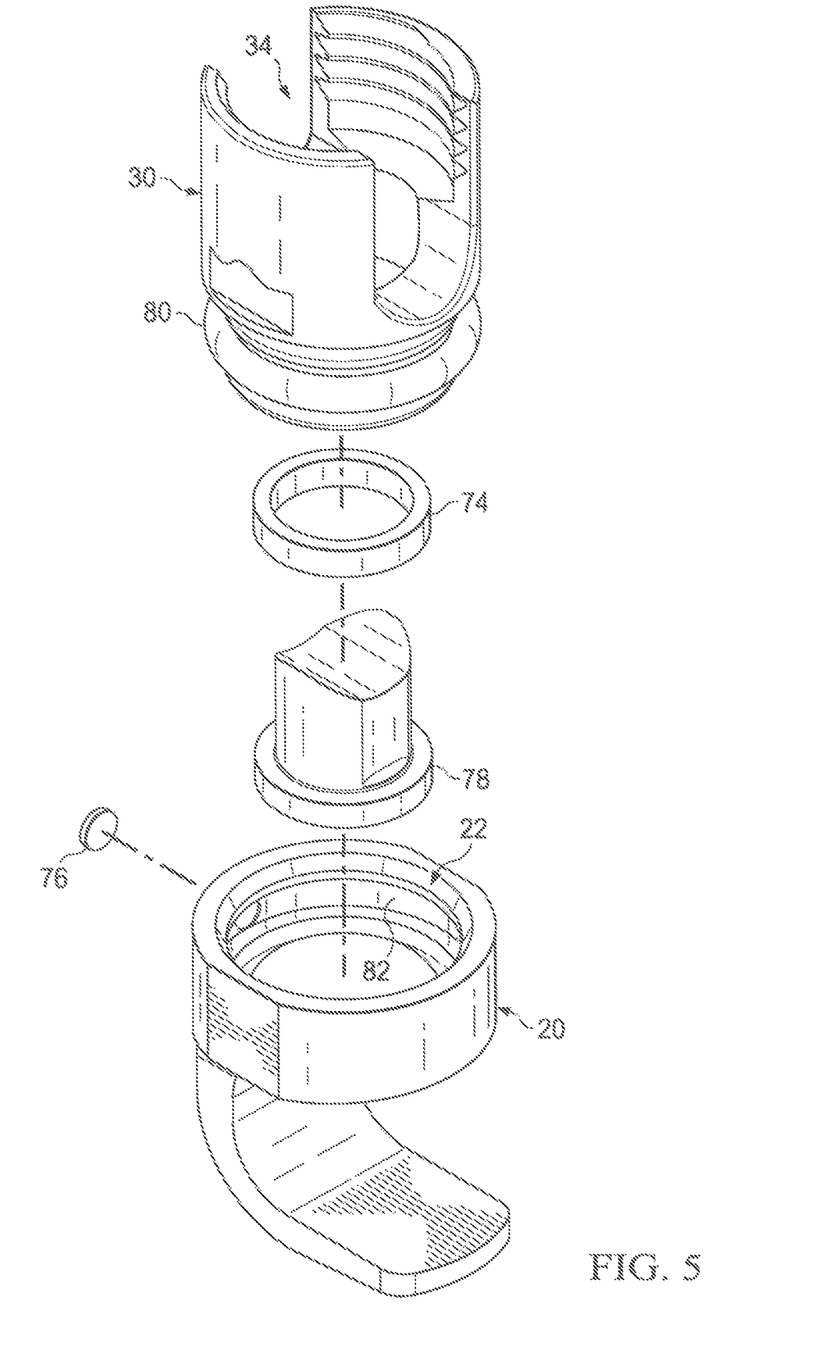
FIG. 5 illustrates a partially exploded view of the surgical hook apparatus of FIG. 4.

In another embodiment of the apparatus 10 according to the present disclosure, rotational mounting of the hook 20 and saddle 30 members is accomplished through employment of a gasket 80, as shown in FIGS. 4 and 5. In such an embodiment, a channel 82 sized to the gasket is defined within the cavity 22 in a manner similar to that discussed above with respect to the ball-based embodiment. Similarly, the channel 82 may be made up of more channel portions 82A, 82B defined in each of the hook 20 and saddle 30 members. The gasket 80 is positioned within the channel 22 in sliding engagement with the hook member 20 and the saddle member 30 so as to rotatably mount those two components to one another so as to allow rotation of the type discussed herein and shown, for example, by the arrows A and B in FIG. 1.

In some embodiments, the saddle member 30 has defined therein a connecting cavity 34 as illustrated in FIGS. 1-3. The cavity 34 has walls 36 that are provided with threads 38 or otherwise configured to engage and retain therein the connecting member 50. If threaded, as shown in FIGS. 1 and 2, such threads 38 engaged complementary threads 62 on the connecting member 50. Alternatively, or in addition, a through hole 40 may be provided in the saddle member 30, through which a set screw 42 is mounted so as to bear against the connecting member in the saddle cavity when the set screw 42 is tightened. While shown, for example, in FIG. 6 as attached to the saddle member 30 so as to initially extend therefrom parallel to the common axis A-A, it will be appreciated that the connecting member 50 could be joined at angles not parallel to such axis A-A. For example, it may be normal to that axis or otherwise oriented to meet the demands of the particular surgical scenario. Further, while shown as extending from a portion of the saddle member 30 distal from the hook member 30, the positioning of the connecting member 50 need not be so limited.

Embodiments of the apparatus 10 disclosed herein may also include a second body 14, similarly featured to the other body 12 and joined to the second end 54 of the connecting member 50.

Embodiments of the present disclosure may be assembled as follows, and looking to the partially exploded view provided in FIG. 3: the spring 74 is inserted onto a pressure cap 78 which is then inserted into the saddle member 30. These components are inserted into the cavity 22 of the hook member 20 and the spring 74 is compressed while the balls 70 are inserted through an opening 79 in the hook member 20 into individual pockets 77 accessible through the channel 72. The hook member 20 and saddle member 30 are rotated relative to each other to facilitate adding balls 70 into each of the pockets 77. Once all the balls 70 are in place the force applied to compress the spring 74 is removed and the spring 74 forces the balls 70 within the portion of the channel 72 defined within the hook member 20. The opening 79 is then sealed by welding the plug 76 in place, as shown in FIG. 2. The spring 74 is compressed between the pressure cap 78 and saddle member 30. This results in a friction fit between the pressure cap 78, saddle member 30, and hook member 20. Light force is required to rotate the hook member 20 relative to the saddle member 30.

In use of embodiments according to the present disclosure, hooks 24 on the hook member 20 can be joined to rods 90 by tightening set screws 92 provided in a through hole 94 defined in the hook member 20, as shown in FIG. 6. Tightening such set screws 92 compresses the pressure cap 78, which in turn applies force to the hook member 20, further compressing the balls 70 between the pockets 77 in the saddle member 30 and the hook member 20. This serves to secure the hook member 20 to the rod 90 as well as locking the position of the hook member 20 relative to the saddle body 30, if sufficient force is applied.

Figure 8:
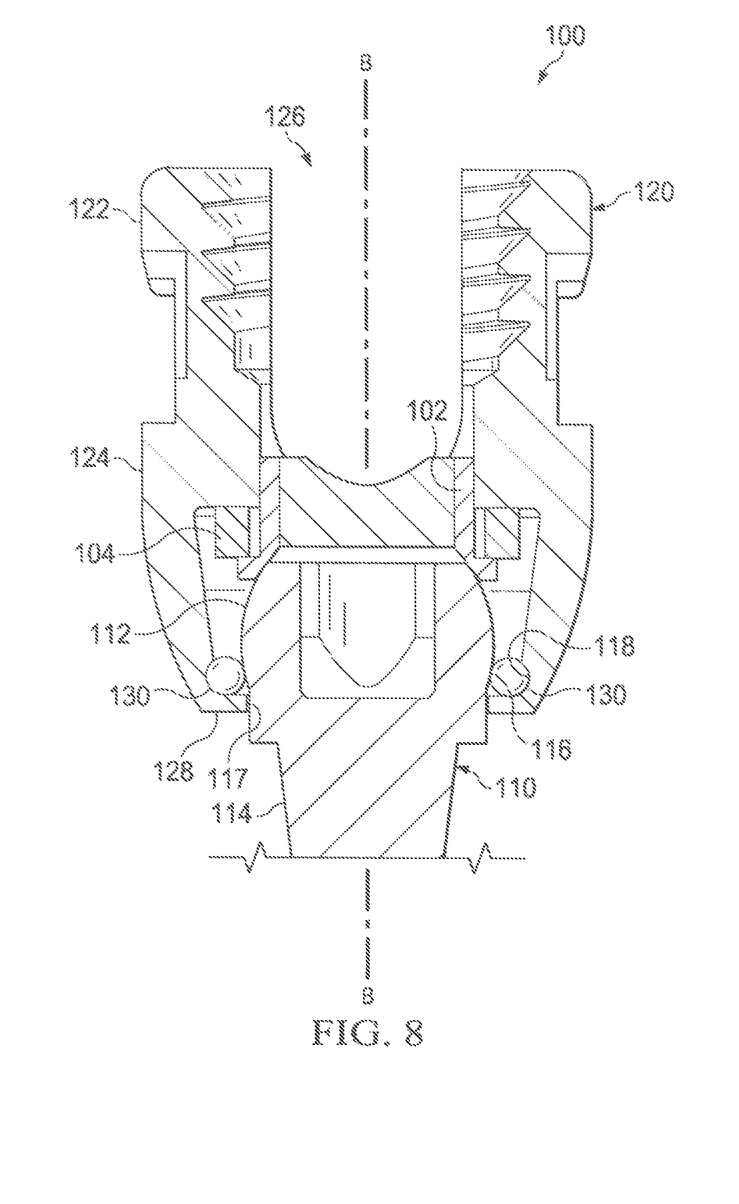
FIG. 8 illustrates a sectional view of an exemplary surgical screw system.

A surgical screw system 100 is shown in FIG. 8. The system 100 includes a screw member 110 having a head portion 112, a body portion 114 and a longitudinal axis B-B. The system 100 also includes a receiver member 120 that has an upper portion 122 and a lower portion 124. The upper portion has a receiving slot 126 defined therein for receiving a surgical rod 128 (shown in FIG. 9).

In an embodiment according to the present disclosure, the receiving member is provided with a plurality of balls 130 embedded in its surface as shown in FIG. 8 and arranged for sliding engagement with the head portion 112 of the screw member 110. The receiving member 120 is removably mountable to the screw member 110 by application of a force substantially parallel to the longitudinal axis of the screw member 110. Also shown in FIG. 8 is a pressure cap 102 and a biasing member 104, such as a coiled spring or a wave spring. The pressure cap 102 and biasing member 104 keep the head portion 112 of the screw member 110 in place after receiving member 120 is attached to the head portion 112 of the screw member 110. The modular nature of the system 100, with the receiving member 120 not being unitarily formed with the screw member 110 or permanently affixed thereto allows for implantation of the screw member 110 in advance of attachment of the receiving member 120. This is advantageous since it allows the practitioner to more easily manipulate the screw member 110 and position it at a desired site, depth and angle of installation without the interference of the receiving member 120 in the way of a driver. Subsequent installation of the receiving member 120 provides added flexibility in terms of placing the surgical rod 128 to be retained therein. This provides balance between the strength of pedicle screws without any adjustability and the relative weakness of multi-axial screws.

When mounted to the head portion 112 the balls 130 are positioned so as to slide about a receiving surface 116 of the head portion 112. The balls 130 engage the receiving surface 116 snugly so as to restrain against movement of the receiving member 120 other than rotation thereof about the longitudinal axis B-B. In addition, the bottom portion 128 of the receiving member 120 remains flush with a bottom portion 117 of the head portion 112, thus restraining the movement of the receiving member 120 other than rotational movement about the longitudinal axis B-B. A complementary receiving channel 118 is provided defined in the receiving surface 116 to facilitate snug engagement of the balls 130 when the receiving member 120 is mounted on the head portion 112. It will be appreciated that various geometries of screw member 110 and head portion 112 could be employed, with the receiving member 120 being sized and shaped to engage therewith in the manner discussed herein to achieve the type of single plane rotation also discussed herein.

Figure 9:
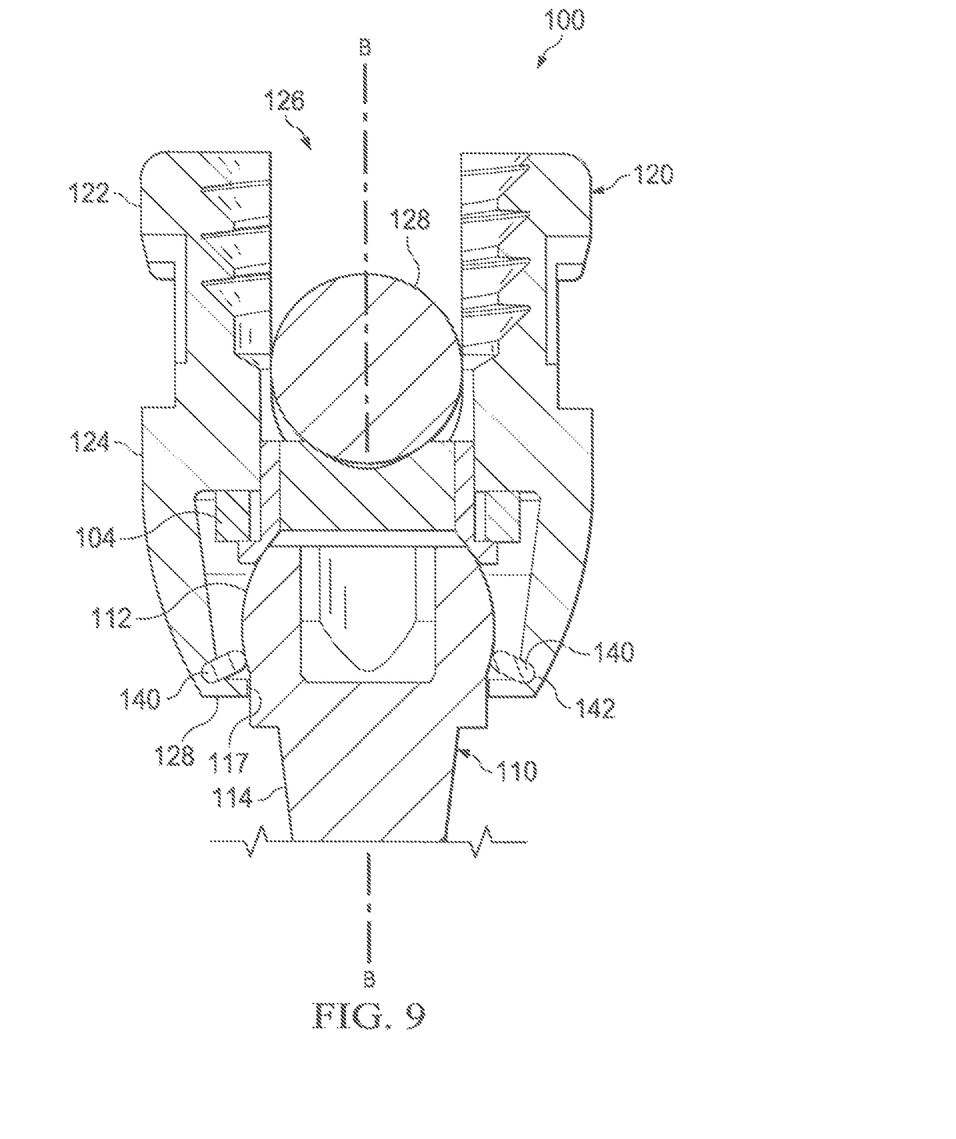
FIG. 9 illustrates a sectional view of another exemplary surgical screw system.

In another embodiment according to the present disclosure, the head portion 112 and receiving member 120 may engage one another via an annular gasket 140, as shown in FIG. 9. This embodiment includes a channel 142 sized to the gasket 140 (or vice versa) and defined by one alone or collectively between the surfaces the receiving member 120 and the head portion 112. The receiving member 120 is mountable to the screw member 110 as discussed above, so as to frictionally engage the gasket 140 with a receiving surface of the screw member 140, for similar single plane only rotation about the longitudinal axis B-B. Much like the embodiment described in FIG. 8, the bottom portion 128 of the receiving member 120 remains flush with a bottom portion 117 of the head portion 112, thus restraining the movement of the receiving member 120 other than rotational movement about the longitudinal axis B-B.

Figure 10:
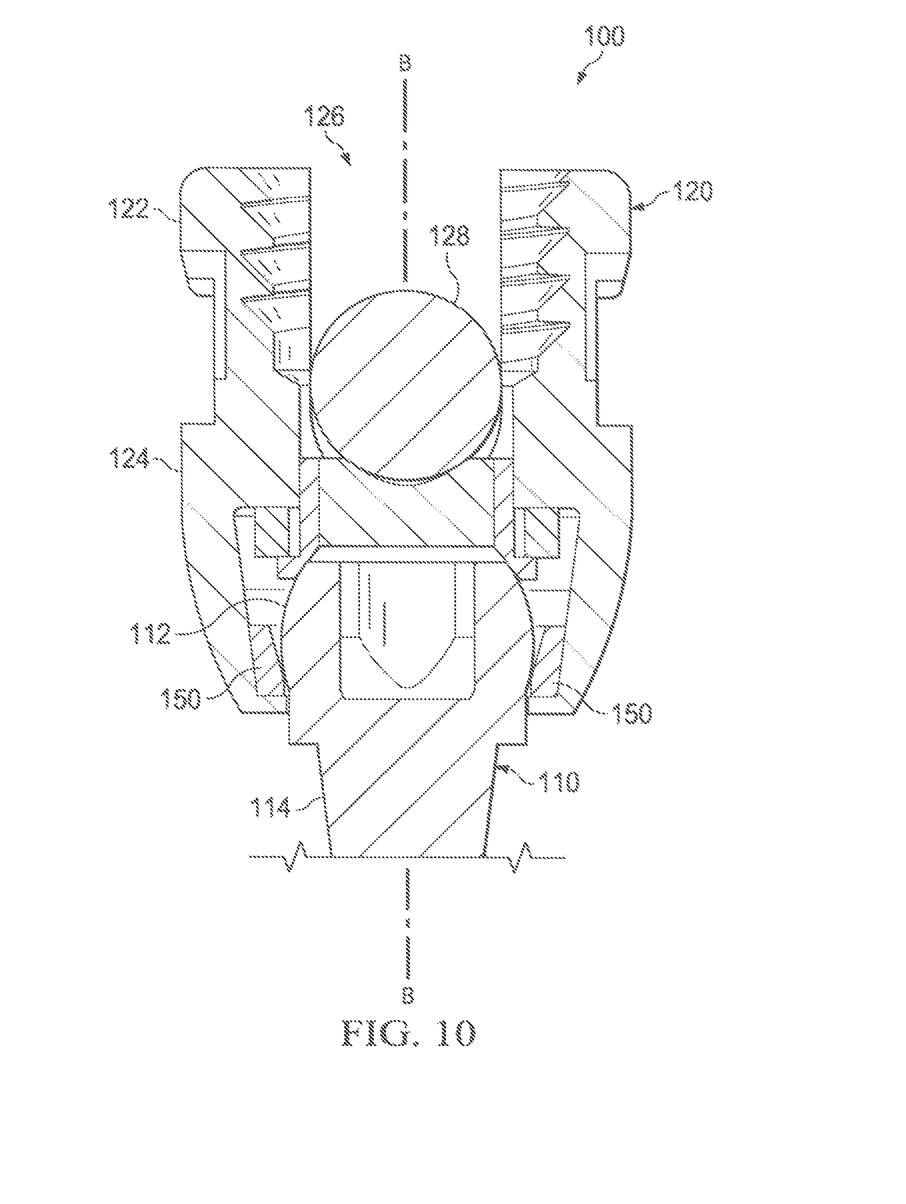
FIG. 10 illustrates a section view of another exemplary surgical screw system.

In another embodiment according to the present disclosure, the head portion 112 and receiving member 120 may engage one another via an annular retaining ring 150, as shown in FIG. 10. The annular retaining ring 150 will flex radially when the receiving member 120 is pressed onto the head portion 112. Much like the embodiment described in FIG. 8, the bottom portion 128 of the receiving member 120 remains flush with a bottom portion 117 of the head portion 112, thus restraining the movement of the receiving member 120 other than rotational movement about the longitudinal axis B-B.

While various embodiments in accordance with the disclosed principles have been described above, it should be understood that they have been presented by way of example only, and are not limiting. Thus, the breadth and scope of the invention(s) should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically and by way of example, although the headings refer to a "Technical Field," such claims should not be limited by the language chosen under this heading to describe the so-called technical field. Further, a description of a technology in the "Background" is not to be construed as an admission that technology is prior art to any invention(s) in this disclosure. Neither is the "Summary" to be considered as a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings herein.

What is claimed is:

1. A surgical screw system, comprising:
   a screw member having a head portion, a body portion and a longitudinal axis;
   a receiver member having upper and lower portions;
   wherein the upper portion is provided with a receiving slot defined therein for receiving a surgical rod;
   wherein the receiver member is provided with a retaining means for engagement with the head portion of the screw member;
   wherein the receiver member is mountable to the screw member by application of a force in a direction parallel to the longitudinal axis and towards the body portion so as to engage the retaining means with a receiving surface of the screw member;
   and wherein when mounted to the head portion the retaining means and receiver member are positioned to slide about the receiving surface to allow rotation of the receiver member about only the longitudinal axis of the screw member and prevent other translational or rotational movement of the receiver member relative to the screw member.

2. The surgical screw system of claim 1, wherein the retaining means comprises an annular gasket, wherein a channel sized to the gasket is defined within a surface of one or more of the receiver member and the head portion, and wherein when mounted to the head portion, the gasket is positioned to slide about the receiving surface of the screw member to permit rotation of the receiver member about only the longitudinal axis of the screw member but prevent all other translational or rotational movement of the receiver member relative to the screw member.

3. The surgical screw system of claim 1, wherein the retaining means comprises an annular retaining ring.

4. The surgical screw system of claim 1, further comprising a biasing member disposed between the receiver member and head portion, the biasing member being arranged to apply a retention force between the receiver member and head portion when the receiver member is mounted to the head portion.

5. The surgical screw system of claim 4, wherein the biasing member is a coil spring or wave spring.

6. A surgical screw system, comprising:
a screw member having a head portion, a body portion and a longitudinal axis;
a receiver member having an upper portion, a lower portion, and a bottom;
wherein the upper portion is provided with a receiving slot defined therein for receiving a surgical rod;
a pressure cap engaged with the head portion of the screw and disposed to engage the surgical rod when the surgical rod is received in the slot;
a retaining means disposed between the head portion of the screw member and the bottom of the receiver member; and
a biasing member biasing the pressure cap toward the head portion of the screw member and biasing the head portion toward the retaining means, the retaining means and receiver member being configured to allow rotation of the receiver member about only the longitudinal axis of the screw member and prevent other translational or rotational movement of the receiver member relative to the screw member.

7. The surgical screw system of claim 6, wherein when mounted to the head portion the retaining means is positioned to slide about a portion of the screw member to allow the receiver member to rotate only about the longitudinal axis of the screw member, and to prevent other translational or rotational movement of the receiver member relative to the screw member.

8. The surgical screw system of claim 6, wherein the retaining means comprises an annular gasket, wherein a channel sized to the gasket is defined within a surface of one or more of the receiver member and the head portion, and wherein when mounted to the head portion, the gasket is positioned to slide about a receiving surface of the screw member, the gasket and receiver member permitting rotation of the receiver member about only the longitudinal axis of the screw member but restraining against all other translational or rotational movement of the screw member.

9. The surgical screw system of claim 6, wherein the retaining means comprises an annular retaining ring.

10. The surgical screw system of claim 6, wherein the biasing member is a coil spring or wave spring.

11. A surgical screw system, comprising:
a screw member having a head portion, a body portion and a longitudinal axis;
a receiver member having an upper portion and a lower portion;
wherein the upper portion is provided with a receiving slot defined therein for receiving a surgical rod;
an annular engagement feature engaged with one of an exterior surface of the head portion of the screw member and an interior surface of the receiver member;
wherein at least one of the receiver member and the head portion comprises an annular channel or annular receiving surface for engagement with the annular engagement feature;
wherein the receiver member is mountable to the screw member by application of a force in a direction parallel to the longitudinal axis and towards the body portion so as to engage the annular engagement feature with the annular channel or annular receiving surface;
and wherein when the head portion is mounted to the receiver member, the annular engagement feature is positioned to slide about the annular channel or annular receiving surface, the receiver member and annular engagement feature being configured to allow rotation of the receiver member about only the longitudinal axis of the screw member and prevent other translational or rotational movement of the receiver member relative to the screw member.

12. The surgical screw system of claim 11, wherein the annular engagement feature comprises an annular gasket.

13. The surgical screw system of claim 11, wherein the annular engagement feature comprises an annular retaining ring.

14. The surgical screw system of claim 11, further comprising a biasing member or compression member situated between the receiver member and head portion, that applies a retention force between the receiver member and head portion when the receiver member is mounted to the head portion.

15. The surgical screw system of claim 14, wherein the biasing member or compression member is a coiled spring or wave spring.

* * * * *